United States Patent
Marissen et al.

(10) Patent No.: US 9,260,801 B2
(45) Date of Patent: Feb. 16, 2016

(54) PROCESS FOR REMOVING RESIDUAL SPIN SOLVENT FROM A GEL SPUN FILAMENT, THE FILAMENT, MULTI-FILAMENT YARN AND PRODUCTS COMPRISING THE FILAMENT

(75) Inventors: Roelof R. Marissen, Born (NL); Claudia Maria C. M. Vaz, Maastricht (NL); Carina Sacha C. S. Snijder, Sittard (NL); Joseph Arnold Paul Maria J A P M Simmelink, Cadier en Keer (NL); Leonard Josef Arnold L. J. A. Nielaba, Eygelshoven (NL)

(73) Assignee: DSM IP ASSETS B.V., Heerlen (NL)

( * ) Notice: Subject to any disclaimer, the term of this patent is extended or adjusted under 35 U.S.C. 154(b) by 1002 days.

(21) Appl. No.: 12/593,469

(22) PCT Filed: Mar. 21, 2008

(86) PCT No.: PCT/EP2008/002298
§ 371 (c)(1),
(2), (4) Date: Dec. 7, 2009

(87) PCT Pub. No.: WO2008/116613
PCT Pub. Date: Oct. 2, 2008

(65) Prior Publication Data
US 2010/0086781 A1 Apr. 8, 2010

(30) Foreign Application Priority Data
Mar. 27, 2007 (EP) .................................... 07006238

(51) Int. Cl.
*D01F 13/04* (2006.01)
*D01F 6/04* (2006.01)

(52) U.S. Cl.
CPC *D01F 6/04* (2013.01); *D01F 13/04* (2013.01); *Y10T 428/298* (2015.01)

(58) Field of Classification Search
CPC ........ B29C 35/0227; D01F 13/04; D01F 6/04
USPC ................ 428/176.1, 204, 205, 210.7, 210.8, 428/211.12, 211.13, 211.14, 211.15, 211.2; 422/33
See application file for complete search history.

(56) References Cited

U.S. PATENT DOCUMENTS 4,027,406 A * 6/1977 Salvatore ........................ 36/83
5,449,745 A * 9/1995 Sun et al. ...................... 528/483

(Continued)

FOREIGN PATENT DOCUMENTS

EP 1 746 187 1/2007
JP 4-209817 7/1992

(Continued)

OTHER PUBLICATIONS

International Search Report for PCT/EP2008/002298, mailed Jun. 18, 2008.

*Primary Examiner* — Andrew Piziali
(74) *Attorney, Agent, or Firm* — Nixon & Vanderhye P.C.

(57) ABSTRACT

Process for removing residual spin solvent from a gel spun, UHMwPE filament having an effective diameter of above 16 µm, comprising the steps of: removing residual spin solvent from the filament to a level of below 100 ppm at elevated temperature, while keeping the filament taut. The invention also relates to gel spun UHMwPE filament having an effective diameter of above 16 µm and a residual spin solvent residue of less than 100 ppm. Preferably the filament has a creep rate, measured at 50° C., under a load, so that the initial stress is 600 MPa, of less than $510^{-6}$ sec$^{-1}$.

18 Claims, 1 Drawing Sheet

(56) References Cited

U.S. PATENT DOCUMENTS

| | | | |
|---|---|---|---|
| 6,361,551 B1 * | 3/2002 | Torgerson et al. | 606/214 |
| 6,951,685 B1 * | 10/2005 | Weedon et al. | 428/364 |
| 2005/0089677 A1 * | 4/2005 | Marissen et al. | 428/299.1 |
| 2006/0012069 A1 * | 1/2006 | Smit et al. | 264/165 |
| 2007/0154707 A1 | 7/2007 | Simmelink et al. | |
| 2008/0287990 A1 | 11/2008 | Smit | |

FOREIGN PATENT DOCUMENTS

| | | |
|---|---|---|
| JP | 2007-522351 | 8/2007 |
| JP | 2008-508003 | 3/2008 |
| WO | 01/73173 | 10/2001 |
| WO | 2005/066401 | 7/2005 |
| WO | 2006/010522 | 2/2006 |
| WO | WO 2006040190 A1 * | 4/2006 |

* cited by examiner

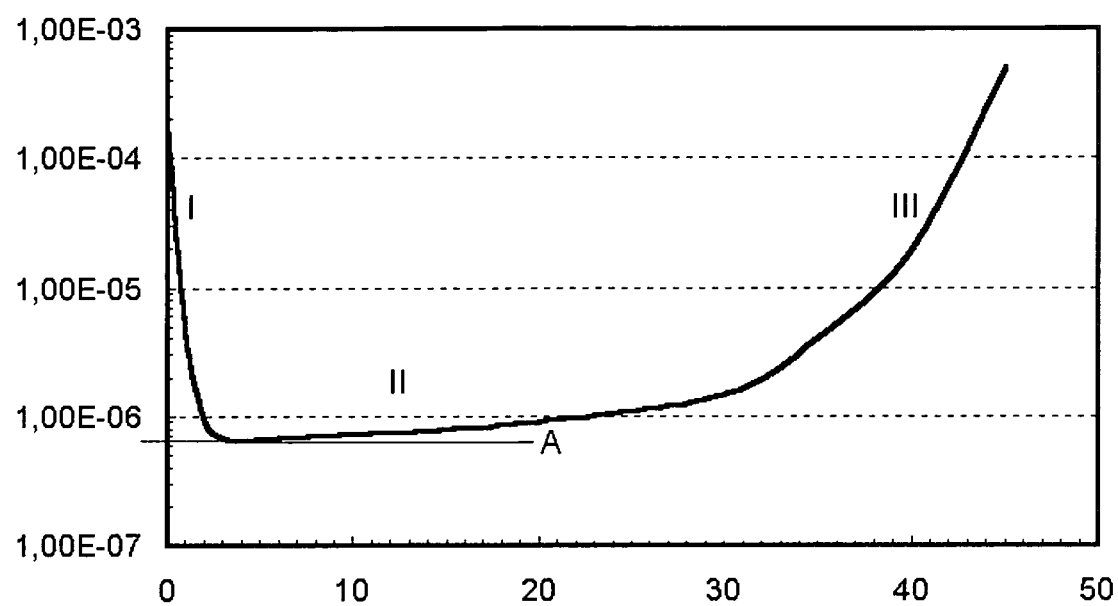

PROCESS FOR REMOVING RESIDUAL SPIN SOLVENT FROM A GEL SPUN FILAMENT, THE FILAMENT, MULTI-FILAMENT YARN AND PRODUCTS COMPRISING THE FILAMENT

This application is the U.S. national phase of International Application No. PCT/EP2008/002298, filed 21 Mar. 2008, which designated the U.S. and claims priority to European Application No. 07006238.5, filed 27 Mar. 2007, the entire contents of each of which are hereby incorporated by reference.

The invention relates to a process for removing residual spin solvent from a gel spun, ultra high molecular weight UHMwPE (UHMwPE) filament, the filament as well as a multi-filament yarn and products for medical applications containing the filament.

A process for producing gel spun, UHMwPE filaments is for example disclosed in PCT/NL2003/000872.

It is also known to use gel spun, UHMwPE multi-filament yarn in products for medical applications. Examples of such products are sutures and cables. Good examples of such cables include a trauma fixation cable, a sternum closure cable, a prophylactic or periprosthetic cable, a long bone fracture fixation cable, a small bone fracture fixation cable. Gel spun UHMwPE multi-filament yarns are suitable for use in such applications, since they have favorable mechanical properties like a high modulus and a high tensile strength. A gel spun filament however has the draw back that without special treatment it contains residual spin solvent. Although the level of residual spin solvent normally is very low, it is still high enough to make the filament less suitable for use in medical applications like sutures and cables, since the residual spin solvent may cause unwanted reactions of the human or animal body, like for instance inflammations. Therefore special treatments are required to decrease the level of residual spin solvent in the filament to a very low level, at least below 100 ppm, preferably however to a still lower level.

Special treatments to remove residual spin solvent include extended extraction or heating of the filament. Problems that occur because of such treatments are that filament properties are adversely affected, if a residual spin solvent level of at most 100 ppm is obtained, but even more if very low levels of residual spin solvent are obtained, below 80 ppm or even further down. This is especially true if filaments with a high diameter are used, since removal of solvents by extraction or evaporation becomes increasingly difficult with increasing diameter. However the use of filaments having a high diameter is advantageous, since such filaments are easier to produce. Furthermore, filaments having a high diameter are more robust during handling (for example with regard to friction) by a surgeon and more abrasion resistant. One of the properties that is adversely affected is the tensile strength of the yarn. This is important since the filaments are mostly applied in products that have to withstand a high tension. Furthermore the smoothness of the surface of the filament may be adversely affected, so that the coefficient of friction of the filament increases. This makes it for example more difficult to stitch a wound with a suture comprising the filament. Also the creep rate of the filament increases. A low level of creep is especially important if the filament is used under tension for a long period at elevated temperature in the body, for example as a sternum closure or a bone fracture fixation cable.

It is therefore an object of the present invention to provide a process for removing residual spin solvent from a gel spun UHMwPE filament having an effective diameter of at least 16 μm, which process provides a filament that not only contains a low level or even no measurable amount of spin solvent residues, but also does not show one or more of the above-identified problems.

This object is achieved according to the invention with a process for removing residual spin solvent from a gel spun UHMwPE filament having an effective diameter of above 16 μm, characterised in that the process comprises the step of: removing residual spin solvent from the filament to a level of below 100 ppm at elevated temperature, while keeping the filament taut.

IN WO 2005/066401, examples 29 and 30 a process is disclosed for spinning an UHMwPE filament, which filament contains less than 100 ppm residual spin solvent. However the filament has a very low diameter of below 8 μm and no special process step for removing residual spin solvent is disclosed.

With the process of the present invention an UHMwPE filament is obtained that has a very low or no measurable amount of solvent residues and yet shows favourable properties. The UHMwPE filaments have a high tensile strength and a low creep rate. Furthermore the filaments have a smooth surface. Therefore the filaments are very suited for use in products for medical applications.

The process for making a gel spun, UHMwPE filament according to the invention comprises the steps of
a) spinning a filament or a plurality of filaments from a solution of UHMwPE in a spin solvent;
b) cooling the filaments obtained to form gel filaments;
c) removing part of the spin solvent from the gel filaments;
d) drawing the filaments in at least one drawing step before, during or after removing part of the spin solvent;
e) removing the residual spin solvent to a level of below 100 ppm.

The filament used in the process according to the invention may comprise any of the known solvents for gel spinning of UHMwPE. Suitable spin solvents include for example paraffin's, like paraffin oil and paraffin wax, mineral oil, kerosene, decalin, tetralin, toluene, lower n-alkanes, for example hexane, xylene, paraxylene, squalane, cyclo-octane. Preferably decalin is used. Cooling of the filament into a gel filament may be performed with a gas flow, or by quenching the filament in a liquid cooling bath. The removal of part of the spin solvent in step c) may be performed by known methods, for example by evaporating a relatively volatile solvent, or by using an extraction liquid. Preferably decalin is used and removed by evaporating.

The process for making an UHMwPE filament comprises drawing the filament in at least one drawing step. Drawing, that is elongating the filament, generally results in at least partial orientation of the polymer molecules and in better mechanical properties of the filaments. Drawing may be performed on a semi-solid or gel-like filament, after cooling down the filament to below the gelation temperature of the solution, or on a solid filament after cooling and removal of solvent. Preferably, drawing is performed in more than one step, e.g. on filaments in gel and/or solid state, and/or at different temperatures.

Preferably the filament used in the process according to the invention contains at the start of the final step (e) of removing the residual spin solvent a level of residual spin solvent of between 100 and 2000 ppm (parts per million by weight). In this way the final filament may be obtained with very low levels of residual spin solvent, still showing favourable properties. More preferably at the start of the step (e) of removing the residual spin solvent the level of residual spin solvent in the filament is below 1500 ppm, even more preferably below 1000 ppm. Preferably at the start of the step of removing the residual spin solvent the filament contains a level of residual spin solvent of more than 200 ppm, even more preferably more than 300 ppm.

Surprisingly it was found that keeping the filament taut in the step of removing the residual spin solvent, a superior filament was realized. By keeping the filament taut is herein meant that a tension in the length direction of the filament is present. The tension may be applied simply by winding the filament, preferably as a multi- or mono-filament yarn taut around a frame. When because of the elevated temperature in the step of removing residual spin solvent the filament yarn tends to shrink, further tension may be build up in the filament. It is also possible to actively apply a tension to the filament, for example by connecting the two ends of the filament to a device and applying a force to the filament by pulling at one or both ends of the filament or by moving the filament through an inline treatment station under tension. The required and the optimum tension depend on the actual design of the treatment station and for the individual design it may be determined empirically by trial and error. When the filament is treated when taut around a frame, it is preferred that the tension is sufficient to prevent the filament to slide on the frame during treatment. In one embodiment, the tension should be above 0.15 g/dtex and preferably the tension should be above 0.30 g/dtex. The tension should be sufficiently low to prevent damage of the filament and the frame. The maximum allowed tension depends to a very large extent on the design of the treatment station and may be determined empirically by trial and error.

Preferably the temperature in the step of removing residual spin solvent is above 80° C., more preferably above 90° C., even more preferably above 100° C. Preferably the temperature in the step of removing the spin solvent is below 140° C., more preferably below 130° C., even more preferably below 125° C.

Preferably the step of removing residual spin solvent is carried out in an environment having an oxygen content of less than 3 mol/m$^3$, more preferably of less than 2 mol/m$^3$, more preferably of less than 1 mol/m$^3$, even more preferably of less than 0.5 mol/m$^3$, most preferably of less than 0.2 mol/m$^3$.

In one preferred embodiment the step of removing residual spin solvent is carried under a reduced air pressure, so that the environment contains above-referred contents of oxygen.

In another preferred embodiment the step of removing residual spin solvent is carried out by subjecting the filament to super critical $CO_2$ extraction. This is because the process runs fast, very low levels of residual spin solvent can be obtained and the properties of the filament remain at a very high level. Especially good results are obtained by subjecting the filament to super-critical $CO_2$ extraction at a temperature between 80 and 147.5° C. and a pressure between 50 and 400 bar, more preferably between 110 and 130° C. and a pressure between 100 and 400 bar.

In this way a filament is obtained that still shows very good mechanical properties and surface smoothness of the filaments and yet containing a very low level of spin solvent. Still further lowering the spin solvent content, while still obtaining a filament with the desired properties is possible by extending the time of the critical $CO_2$ extraction step and/or by choosing a temperature closer to 130° C. Therefore the temperature is preferably chosen between 120 and 130° C. The time interval for the filament treatment may simply be determined by taking samples at different time intervals during the extraction process, determining the level of residual spin solvent and comparing the determined level of residual spin solvent with the desired level. Typical extraction times vary between half an hour and 24 hours, depending on desired level of residual spin solvent, temperature and further process parameters.

Preferably the time interval for the filament treatment and the temperature are chosen in a way that the final residual spin solvent content is less than 80 ppm, more preferably below 60 ppm, still more preferably below 40 ppm, most preferably below 30 ppm.

The process according to the present invention is applied to a filament having an effective diameter above 16 μm. Within the context of the present application, the effective diameter is understood to be the averaged maximum cross-sectional dimension of the filaments. For filaments having a circular cross-section and an effective diameter of 16 μm the titer is about 1.96 dtex. Preferably the filament has a titer of between 2-100 dtex, more preferably between 2-30 dtex, such as 2-5 dtex or even 2-3 dtex. In another embodiment, the effective diameter of the filament has an effective diameter of above 18 μm and preferably the filament has an effective diameter of above 25 μm, such as an effective diameter of above 75 μm. The higher thickness of filaments are typically utilised for mono-filament applications whereas lower diameters typically would be utilised in multi-filament yarns.

Preferably in the process according to the invention the filament does not contain spin finish. It is possible that the spin finish, if present, is removed from the gel spun UHMwPE filament, before the step of removing the residual spin solvent is carried out. Spin finish may be removed by the process described in PCT/NL2003/000872. In that case residual spin solvent is removed fast and to a very low level, while maintaining the properties of the filament.

In the process according to the invention the filament is preferably present as a multi-filament yarn. It is however also possible that the filament is present in a product containing the multi-filament yarn, for example a suture, a cable, a weft or any further article, provided that the filaments are kept taut.

In another embodiment of the process according to the invention, the filament is a mono-filament. Monofilaments are preferred by surgeons in some cases where compactness is more important than flexibility, for example for some sutures.

The invention also relates to a gel spun UHMwPE filament having a diameter of above 16 μm and a level of residual spin solvent of less than 100 ppm. The invention also relates to a multi-filament yarn comprising such a filament as well as a mono-filament consisting of one such a filament.

In one embodiment, the filament has a creep rate at 50° C., measured by applying a load to the filament so that the initial tensile stress in the filament is 600 MPa, of less than $5 \cdot 10^{-6}$ sec.$^{-1}$, more preferably of less than $8 \cdot 10^{-6}$ sec.$^{-1}$, most preferably of less than $10^{-7}$ sec.$^{-1}$.

Preferably, the UHMwPE applied in the filament is a linear UHMwPE, i.e. an UHMwPE with less than one side chain or branch per 100 carbon atoms, and preferably less than one side chain per 300 carbon atoms, a branch generally containing at least 10 carbon atoms. The UHMwPE may further contain up to 5 mol % of or more alkenes that can be copolymerized with it, such as propylene, butene, pentene, 4-methylpentene or octene.

Preferably, the UHMwPE has an intrinsic viscosity (IV) of more than 5 dl/g. The IV is a measure for the weight average molecular weight of the UHMwPE. Filaments made from such UHMwPE have very good mechanical properties, such as a high tensile strength, modulus, and energy absorption at break. More preferably, an UHMwPE with an IV of more than 10 dl/g is chosen. Such gel-spun UHMwPE filaments offers a combination of high strength, low relative density, good hydrolysis resistance, and excellent wear properties, making it suited for use in various biomedical applications, including implants. The IV is determined according to method PTC-179 (Hercules Inc. Rev. Apr. 29, 1982) at 135° C. in decalin, the dissolution time being 16 hours, with DBPC as the antioxidant in an amount of 2 g/l solution, and the viscosity at different concentrations is extrapolated to zero concentration.

Preferably the gel spun UHMwPE filament according to the invention contains less than 80 ppm residual spin solvent, more preferably less than 60 ppm, still more preferably less than 40 ppm, most preferably less than 30 ppm.

The invention also relates to a multi-filament yarn, containing filaments according to the invention.

Preferably the gel spun, UHMwPE multi-filament yarn according to the invention has a tenacity of at least 3.4 N/tex, more preferably at least 3.6 N/tex, even more preferably 3.8 N/tex, most preferably 4.0 N/tex.

The invention also relates to products for medical application comprising the gel spun UHMwPE multi-filament yarn or monofilament according to the invention. Good examples of such products include sutures and cables, but also endless loop products, bag-like, balloon-like products and other woven and/or knitted products. Good examples of cables include a trauma fixation cable, a sternum closure cable, and a prophylactic or per prosthetic cable, long bone fracture fixation cable, small bone fracture fixation cable. Also tube-like products for ligament replacement are considered.

EXAMPLES

Preparation of Yarn

A commercial grade Dyneema™ SK 75, delivered by DSM Dyneema, the Netherlands, was washed several times with soaps and solvents, until no spin finish could be detected any more.

The amount of residual spin solvent was about 400 ppm. The yarn was treated at elevated temperature to remove spin solvent (step e)) as indicated below.

Measurement of Tensile Strength.

Tensile properties: tensile strength (or strength), tensile modulus (or modulus) and elongation at break (or eab) are defined and determined on multifilament yarns with a procedure in accordance with ASTM D885M, using a nominal gauge length of the fibre of 500 mm, a crosshead speed of 50%/min and Instron 2714 clamps, of type Fibre Grip D5618C. On the basis of the measured stress-strain curve the modulus is determined as the gradient between 0.3 and 1% strain. For calculation of the modulus and strength, the tensile forces measured are divided by the titre, as determined by weighing 10 meters of fibre; values in GPa are calculated assuming a density of 0.97 g/cm³. Strength of braided members was measured (after tying one simple knot) on a Zwick 1435 apparatus with Instron 1497 K clamps.

Measurement of Creep Level.

The creep is measured by placing a piece of the yarn in a hot air oven at 50° C., connecting one end of the yarn by winding it several times around a round bar, having a diameter of 10 mm and connecting the other end with a weight, so that at the start of the creep measurement the level of tensile stress is 600 MPa.

The creep behaviour is represented in a plot in which the creep rate is given as a logarithmic function (y-axis) of the total creep deformation (x-axis) in %. In such a plot 3 regions can be observed, as indicated in FIG. 1. Region I (indicated by I in FIG. 1) is finished after a relatively short time and is characterized by a step decrease of the creep rate. Region II (indicated by II in FIG. 1) is characterised with a constant but in most instances slightly increasing creep rate. In Region III (indicated by III in FIG. 1) a rapid increase in creep rate occurs, followed by breaking of the yarn. The creep resistance of the yarn is characterised by the minimum value of the creep rate in the plot, at the start of region II (indicated by A in FIG. 1).

Measurement of Residual Spin Solvent.

The chemical type and wt % of solvent is measured via Dynamic headspace gas chromatography coupled to flame ionization detection (FID) and mass spectrometry detection in series.

The sample measurement is performed as follows:
The sample is cut in 20 mm pieces. 50 mg of the sample is placed in a desorption tube (thermodesorption system (eg. Gerstel™ TDS 2 with an autosampler Gerstel™ TDS A, both delivered by Sigma-Aldrich Inc.), and a cooled injection system (eg. Gerstel™ CIS4, delivered by Sigma-Aldrich Inc.)).

At each side of the sample the tube is filled over about 30 mm with a plug of glass wool. The tube is heated for 30 minutes at 200° C. During heating the sample, a gas-flow of helium, is sent through the tube. The volatiles, components which are vaporized by heating, are trapped on a cold trap, which is cooled with liquid nitrogen, at ±150° C. The cold trap is heated, after 30 minutes of desorption. The components are collected in the cooled injection system and injected with a split ratio of 1:20 and separated on a gas chromatographic column (30 m fused silica (id=0.25 mm), CP-Sil™ 8 CB low bleed/MS) using a gas chromatograph (eg. Hewlett Packard™ system type 6890, delivered by Hewlett Packard in the US).

Detection of the components is performed with a flame ionisation detector (FID) and a mass selective detector (Hewlett Packard 5973 (MSD)).

Determination of the FID peak areas of references and samples are performed for determination of the type and amount of solvent.

Calculation the response factor ($F_c$) for the n-alkanes using the formula I:

$$F_c = C_c/A_c \qquad \text{Form. I}$$

Where:
$A_c$=peak area of n-alkane measured by the calibration
$C_c$=concentration of n-alkane in the calibration solution (µg/0.3 µl)
Calculation of the concentration ($C_s$) in mg/kg using formula II:

$$C_s = A_s * F_c/I_s \qquad \text{Form. II}$$

Where:
$F_c$=response factor, calculated according tot formula I
$A_s$=peak area component measured by the sample analysis
$I_s$=amount of sample (gram)

Comparative Experiment A

Creep and tensile strength of the Dyneema™ SK 75, of which the spin finish was removed were measured according to the methods given above. The results are given in Table 1. The content of residual spin solvent of the yarn was about 400 ppm.

Comparative Experiment B

The Dyneema™ SK 75 yarn of comparative experiment A was kept for 64 hours at 135° C. at 1 atmosphere in air. After the treatment creep, tensile strength and residual spin solvent of the yarn were measured according to the methods given above. The results are given in Table 1. The content of spin solvent is well below 100 ppm, however mechanical properties of the yarn were deteriorated. It was even impossible to perform the creep test, due to immediate breakage of the yarn.

Comparative Experiment C

The Dyneema™ SK 75 yarn of comparative experiment A was kept for 64 hours at 120° C. at 1 atmosphere in air. After the treatment creep, tensile strength and residual spin solvent of the yarn were measured according to the methods given above. The results are given in Table 1. The content of spin solvent is well below 100 ppm, however the tensile strength of the yarn was deteriorated and the creep level was adversely affected.

Experiment 1

The Dyneema™ SK 75 yarn of comparative experiment A was kept for 64 hours at 120° C. The yarn was wound around a frame, so that the yarn was kept taut during the treatment. After the treatment creep, tensile strength and residual spin solvent of the yarn were measured according to the methods given above. The content of residual spin solvent was well below 100 ppm. Further results are given in Table 1. It shows that after the treatment (step e) the level of creep is even lower than the level of the untreated yarn.

Experiment 2

The Dyneema™ SK 75 yarn of comparative experiment A was put in an autoclave, filled with supercritical $CO_2$ at a temperature of 100° C. for one hour. The oxygen content of the super-critical $CO_2$ environment in the autoclave was 1.2 mol/m$^3$. The yarn was wound around a frame, so that the yarn was kept taut during the treatment. After the treatment creep, tensile strength and residual spin solvent of the yarn were measured according to the methods given above. The results are given in Table 1. The content of spin solvent is well below 100 ppm. It shows that after the treatment (step e) the level of creep is comparable to that before the treatment.

| Example/comparative experiment | Tensile sttrength cN/dtex | Minimum creep rate (1/second) |
| --- | --- | --- |
| Comp. Exp. A | 35 | $9.0 \cdot 10^{-7}$ |
| Comp. Exp. B | 3 | Undetectable |
| Comp. Exp. C | 10 | $7.0 \cdot 10^{-6}$ |
| Ex. 1 | 26 | $7.0 \cdot 10^{-7}$ |
| Ex. 2 | 30.5 | $9.5 \cdot 10^{-7}$ |

The invention claimed is:

1. A process for removal of residual spin solvent from a gel spun ultrahigh molecular weight polyethylene (UHMwPE) filament comprising the steps of:
    (a) providing a gel spun UHMwPE filament having an effective diameter of above 16 µm and a residual spin solvent content of between 100 and 2000 ppm,
    (b) winding the gel spun UHMwPE filament provided by step (a) around a frame so that the filament is taut around the frame at a tension of more than 0.15 g/dtex, and subsequently
    (c) placing the frame with the filament wound taut therearound according to step (b) in an autoclave and removing residual spin solvent from the filament by subjecting the filament taut to super critical $CO_2$ extraction in the autoclave at a temperature between 80° C. and 147.5° C. and at a pressure between 50 bar and 400 bar for a time period between half an hour and 24 hours to thereby obtain a UHMwPE filament with residual spin solvent content of below 100 ppm.

2. The process according to claim 1, which comprises providing a gel spun, UHMwPE filament having an effective diameter of above 18 µm.

3. The process according to claim 1, wherein the elevated temperature is above 90° C.

4. The process according to claim 1, wherein the elevated temperature is below 130° C.

5. The process according to claim 1, wherein step (c) is carried out under a reduced air pressure so that the filament is in an environment having an oxygen content of less than 3 mol/m$^3$.

6. The process according to claim 5, wherein the oxygen content of the environment is less than 1 mol/m$^3$.

7. The process according to claim 1, wherein step (c) is practiced such that the spin solvent is removed to a level below 80 ppm.

8. The process according to claim 1, wherein step (c) is practiced such that the spin solvent is removed to a level below 60 ppm.

9. The process according to claim 1, wherein the filament does not contain spin finish when the residual spin solvent is removed according to step (c).

10. The process according to claim 1, wherein step (a) comprises providing a gel spun, UHMwPE filament having an effective diameter of above 25 µm.

11. The process according to claim 1, wherein step (a) comprises providing a gel spun, UHMwPE filament having an effective diameter of above 75 µm.

12. The process according to claim 1, wherein step (a) comprises providing a gel spun, UHMwPE filament having an effective diameter of above 18 µm.

13. The process according to claim 1, wherein step (a) comprises providing a gel spun, UHMwPE filament having a residual spin solvent content of between 200 and 1500 ppm.

14. The process according to claim 1, wherein the filament is a monofilament or a multi-filament yarn.

15. The process according to claim 1, wherein step (b) comprises keeping the filament taut around the frame with a tension of above 0.30 g/dtex.

16. The process according to claim 1, wherein step (c) comprises subjecting the filament to super critical $CO_2$ extraction in an autoclave at a temperature between 110° C. and 130° C. and pressure between 100 bar and 400 bar.

17. The process according to claim 5, wherein the oxygen content of the environment is less than 0.2 mol/m$^3$.

18. The process according to claim 1, wherein the UHMwPE filament with residual spin solvent content of below 100 ppm obtained after step (c) has a tenacity of at least 3.4 N/tex.

* * * * *